(12) United States Patent
Zuidema et al.

(10) Patent No.: US 10,188,807 B2
(45) Date of Patent: Jan. 29, 2019

(54) LOW RESIDUAL VOLUME SYRINGE/CONDUIT COMBINATION AND SYRINGE FOR SUCH A SYRINGE/CONDUIT COMBINATION

(71) Applicant: Linesbridge Pharma Group B.V., Emmen (NL)

(72) Inventors: Tjeerd Zuidema, Emmen (NL); Alexander Christiaan Boudewijn, Emmen (NL); Edwin Alexander Schulting, Emmen (NL); Jan van der Velde, Emmen (NL)

(73) Assignee: Linesbridge Pharma Group B.V., Emmen (NL)

( * ) Notice: Subject to any disclaimer, the term of this patent is extended or adjusted under 35 U.S.C. 154(b) by 645 days.

(21) Appl. No.: 14/413,950

(22) PCT Filed: Jul. 12, 2013

(86) PCT No.: PCT/NL2013/050527
§ 371 (c)(1),
(2) Date: Jan. 9, 2015

(87) PCT Pub. No.: WO2014/011046
PCT Pub. Date: Jan. 16, 2014

(65) Prior Publication Data
US 2015/0157811 A1 Jun. 11, 2015

(30) Foreign Application Priority Data
Jul. 12, 2012 (NL) .................................. 2009180

(51) Int. Cl.
*A61M 5/34* (2006.01)
(52) U.S. Cl.
CPC .............. *A61M 5/346* (2013.01); *A61M 5/34* (2013.01)

(58) Field of Classification Search
CPC .................................. A61M 5/34; A61M 5/346
See application file for complete search history.

(56) References Cited

U.S. PATENT DOCUMENTS

| 4,391,029 A | 7/1983 | Czuba et al. |
| 5,782,803 A * | 7/1998 | Jentzen .............. A61M 5/31511 604/110 |

(Continued)

FOREIGN PATENT DOCUMENTS

| CN | 101015717 A | 8/2007 |
| EP | 0966982 A2 | 12/1999 |

(Continued)

OTHER PUBLICATIONS

"International Application Serial No. PCT/NL2013/050527, Written Opinion dated Oct. 8, 2013", 8 pgs.

(Continued)

*Primary Examiner* — Brandy S Lee
(74) *Attorney, Agent, or Firm* — Schwegman Lundberg & Woessner, P.A.

(57) ABSTRACT

Syringe/conduit combination with a syringe part (1) and a conduit part (2). The parts have a male slip fitting (4) and a female slip fitting (5) for press fitted connection. The syringe part (1) has a hollow barrel (22) and a plunger (23) inserted into the barrel (22). The plunger (23) and the hollow barrel (22) have abutments (25, 27) defining a maximally inserted position of the plunger (23). The male slip fitting (4) fits in the female slip fitting (5) such that the male slip fitting (4) is at an axial distance of less than 0.1 mm from an internal end of the female slip fitting (5). The plunger (23) in its maximally inserted position is then at an axial distance from an opposite one of the slip fittings (5) that is equal to or less than the axial distance between the male slip fitting (4) and the internal end (9) of the female slip fitting (5).

14 Claims, 2 Drawing Sheets

(56) References Cited

U.S. PATENT DOCUMENTS 6,053,894 A * 4/2000 Shadd, Jr. .......... A61M 5/31511
604/110
2011/0028909 A1* 2/2011 Lum ...................... A61M 5/34
604/192

FOREIGN PATENT DOCUMENTS

| WO | WO-9401161 | 1/1994 |
| WO | WO-09530446 A1 | 11/1995 |
| WO | WO-2007006030 A2 | 1/2007 |
| WO | WO-2010126791 A1 | 11/2010 |
| WO | WO-2014011046 A1 | 1/2014 |

OTHER PUBLICATIONS

"International Application Serial No. PCT/NL2013/050527, International Search Report dated Oct. 8, 2013", 3 pgs.
"International Application Serial No. PCT/NL2013/050527, International Preliminary Report on Patentability dated Jan. 13, 2015", 5 pgs.
"Zero Dead Space Syringe", Qosina Thousands of Stock Components, (Sep. 23, 2009), 1 pgs.

* cited by examiner

LOW RESIDUAL VOLUME SYRINGE/CONDUIT COMBINATION AND SYRINGE FOR SUCH A SYRINGE/CONDUIT COMBINATION

PRIORITY APPLICATIONS

This application is a U.S. National Stage Filing under 35 U.S.C. 371 from International Application No. PCT/NL2013/050527, filed on 12 Jul. 2013, and published as WO2014/011046 A1 on 16 Jan. 2014, which claims the benefit under 35 U.S.C. 119 to Netherlands Application No. 2009180, filed on 12 Jul. 2012; which applications and publication are incorporated herein by reference in their entirety.

FIELD AND BACKGROUND OF THE INVENTION

The present invention generally relates to syringe/conduit combinations having a frustoconical male slip fitting and a frustoconical female slip fitting, the male slip fitting being inserted or insertable into the female slip fitting establishing a press fitted connection. The conduit part may for instance be a needle assembly or via which a fluid can be injected into a medical tubing, a bag or a catheter.

Syringes are typically joined to downstream tubing by connecting matching fittings on the distal end of the syringe and a proximal end of the conduit part. One common connector type has matching male and female fittings each having conical surfaces that, when the fittings are connected, provide a sealed press fit connection between tubes. Conical fittings that form a seal by pressing the fittings together are often referred to as "slip fittings" Conical fittings that also include a form locked axial load transfer, such as threaded elements or a bayonet fitting are often referred to as "lock fittings."

Standards have been developed to permit compatibility of standard fittings. An example of specifications for conical fittings used for medical applications may be found, for example, in the International Standard ISO 594-1 titled "Conical fittings with 6% (Luer) Taper for syringes, needles and certain other medical equipment," and referred to herein as the "ISO Luer Standard."

FIGS. 1 through 3 slip fitting conforming to the ISO Luer Standard are shown, where FIG. 1 is a side view of a male slip fitting 10 and a matching female slip fitting 20, and FIG. 2 is a sectional view along the line II-II in FIG. 1.

The male slip fitting 10 has an external frustoconical surface 11 and a distal end 16 for inserting into female slip fitting 20. The female slip fitting 20 has an internal frustoconical surface 21 matching at least a portion of the external frustoconical surface 11 of the male slip fitting 10.

The slip fittings 10 and 20 each have conical surfaces resulting in a conical angle θ, as shown. According to the ISO Luer Standard, the value of this conical angle is 6°. The external frustoconical surface 11 of the male slip fitting 10 has a height A from a proximal base 17 to the distal end 16 having a diameter B. The internal frustoconical surface 21 of the female slip fitting 20 has a depth D extending from an opening with a diameter C to a bottom end 26. The height A, diameters B and C and depth D, are mandated by the ISO Luer Standard, and define contacting surfaces.

FIG. 3 is a sectional view along the line II-II in FIG. 1, but with the male and female slip fittings 10 and 20 connected by applying an axial pressure force of 27.5 N for 5 s whilst twisting action if any is limited to a torque value not exceeding 0.1 Nm to give rotation not exceeding 90°. Such an engagement force is also called an axial engagement force or normalized axial engagement force, and is applied such that a portion of frustoconical surfaces 11 and 21 are in contact, where the contact portion is indicated by the length X. The ISO Luer Standard mandates that the distal end 16 and bottom end 26 be separated by a distance, which is indicated as E=X−D. The value of E is not specified by the ISO Luer Standard, but is required to be greater than zero. In practice, in ISO Luer Standard compliant fittings, the distance E is typically about 2 mm or more and the diameter B is approximately 4 mm, so that, a "dead space" 300 within connected fittings 10 and 20 of approximately 40 μl is left, in addition to the dead space constituted by the channels in the syringe part and in the conduit part. Medicament volumes left in this dead space constitute a waste of medicament and associated costs, in particular when expensive drugs are administered. Medicament leftovers in the dead space may also constitute an environmental and/or health hazard.

Other, functional requirements of the ISO Luer Standard are that after a slip type connection has been made, to prevent inadvertent disconnection, the slip type connection should resist an axial removal force of 35 Newton and unscrewing torque of up to 0.02 Nm without disconnection. In addition, slip type connections should also hold a seal against 3 bar after a connection has been made. In slip fitting connections this resistance and sealing is supplied by the friction between the opposing conical surfaces.

SUMMARY OF THE INVENTION

It is an object of the present invention to provide a syringe/conduit combination in which the dead space between the male and female fittings is reduced, while still allowing a slip connection to be made by axial pressure in conformity with the ISO Luer Standard, ensuring that resistance against dislodgement meets the ISO Luer Standard requirements and without use of additional separate components.

According to the invention this object is achieved by providing a syringe according to claim 1.

By reducing the distance left between the distal end of the male fitting and the inner end of the female fitting to less than 0.1 mm, providing abutments limiting axial displacement of the plunger in a distal direction to a maximally inserted position and providing that, when the male slip fitting is axially inserted into the female slip fitting so that said press fitted connection is established, a distal end of the plunger, when in its maximally inserted position, is at an axial distance from an opposite one of the slip fittings that is equal to or less than the axial distance between the male fitting and the internal end of the female slip fitting, dead space is substantially reduced whereas, as a result of the abutment, it is prevented that the plunger pushes the conduit part off the syringe barrel so that resistance against inadvertent dislodgement is not compromised.

In a preferred embodiment of a syringe/conduit combination according to the invention the distance left between the distal end of the male fitting and the inner end of the female fitting is less than 0.05 mm, most preferably 0.042 mm or less. Such an axial distance further reduces the dead space significantly and can be realized within present day manufacturing tolerances, while meeting the ISO Luer Standard requirements regarding resistance against axial removal forces to prevent inadvertent disconnection after the slip connection has been made.

Preferably, the male slip fitting is axially inserted or insertable into the female slip fitting such that the male slip fitting is in contact with the internal end of the female slip fitting, to further reduce the dead volume. Also in this embodiment, the fittings are dimensioned such that the slip type connection between the male and female slip fitting conforms to the ISO Luer Standard requirements regarding the resistance against inadvertent dislodgement up to a pressure of 3 bar, an axial removal force of 35 Newton and an unscrewing torque of up to 0.02 Nm. Thus, the male slip fitting and the female slip fitting are dimensioned and manufactured of a material which is deformable such that the distal tip of the male slip fitting can be extended into the female slip fitting up to the internal end thereof and generates a sufficiently tight press fit to ensure the required resistance against unwanted dislodgement.

It is further preferred that the male slip fitting has a conical portion and a free end beyond the conical portion, wherein the free end and the internal end of the female slip fitting have matching shapes such that when the free end of the male slip fitting is in contact with the internal end of the female slip fitting, substantially the entire surface of the free end of the male slip fitting is in contact with the internal end of the female slip fitting. The large area over which the axial end surfaces of the fittings are in contact reduce the presence of residual volumes between these axial end surfaces.

For reducing the residual volume even if the axial ends of the fittings are not in contact or if the fitting opposite the plunger has a central portion sloping away from the fitting through which the plunger extends, it is preferred that the plunger in its maximally inserted position projects distally from the fitting of the syringe.

Preferably, the portion of the internal wall bounding the internal cross-section and sealingly fitting around the cross-section of the plunger extends up to the distal end of the syringe. Thus a uniform, constant cross-section channel through which the plunger can be advanced to or even slightly beyond the distal end of the syringe, leaving no dead volume in the syringe including its fitting, can be obtained. The problem of medicament left in a dead volume is typically of particular relevance for medicaments of which small volumes have to be administered and for dosaging such small volumes an essentially single cross-section dosaging channel through which the plunger is displaceable, is particularly suitable. Furthermore, a projecting tip of the plunger for filling up a narrowed distal end of the internal space of the hollow barrel is avoided. Such a projecting tip adds to the complexity of manufacture and can result in a reduced rate of flow of fluid per unit of plunger displacement in a last portion of the stroke of the plunger. At a given plunger pressure this can result in a temporarily increased fluid pressure and an accordingly increased risk of dislodgement of the connection between the fittings. In a further elaboration, the distal face of the plunger has a shape matching the shape of the opposing surface of the opposite slip fitting. Thus, a minimal dead space volume is left.

For a simple construction of the hollow barrel and the plunger, it is advantageous if the abutments limiting axial displacement of the plunger towards the fitting to a maximally inserted position are preferably located proximally of the portion of the internal wall bounding the internal cross-section sealingly fitting around the cross-section of the plunger. If one of the abutments is constituted by the proximal end of the hollow barrel, an end surface that is present anyway also doubles up as the abutment of the hollow barrel for co-operation with the abutment on the plunger which may for instance be provided in the form of a distally facing surface of a flange projecting radially at the proximal end of the plunger.

By providing that either the male slip fitting or the female is dimensioned to fully conform to the ISO Luer Standards, a hybrid design of a syringe/conduit combination is provided in which one fluid transfer device is a conventional part that can be sourced at low cost and widely available allows the use of existing stock of such parts. Preferably, the conduit part has the slip fitting fully conforming to the ISO Luer Standard, so that the special features for reducing dead space without compromising resistance against dislodgement can all be applied to the syringe part and the syringe part can be combined with standard conduit parts such as needle assemblies, connectors etc.

In a particular advantageous embodiment of a syringe/conduit combination according to the invention the frusto-conical surface of the male slip fitting has a taper in the range between about 3° and 4°, preferably about 3.44°. With such a taper, which deviates from the value of 6° as stipulated by the ISO Luer Standard, a reliable press fit connection to an ISO Luer Standard female fitting can be obtained with less variation of the depth of insertion. In particular, compared with a conventional ISO Luer Standard mail slip fitting, a redistribution of the clamping pressure towards the free end of the male fitting is obtained, so that the depth of insertion is to a larger extent limited by the rapidly increasing resistance against deformation of the wall of the female fitting where it connects to the internal end of the female fitting.

The present invention can also be embodied in a syringe according to claim 13, which is specifically adapted for use in a syringe/conduit combination according to the invention.

To further clarify various aspects of embodiments of the present disclosure and additional features and advantages of the embodiments, a more particular description of various aspects and features will be rendered by reference to specific embodiments thereof, which are illustrated in the appended drawings. It is appreciated that these drawings depict only examples and are therefore not to be considered limiting the scope of the disclosure, nor are the figures necessarily drawn to scale.

DETAILED DESCRIPTION

Figure 1:
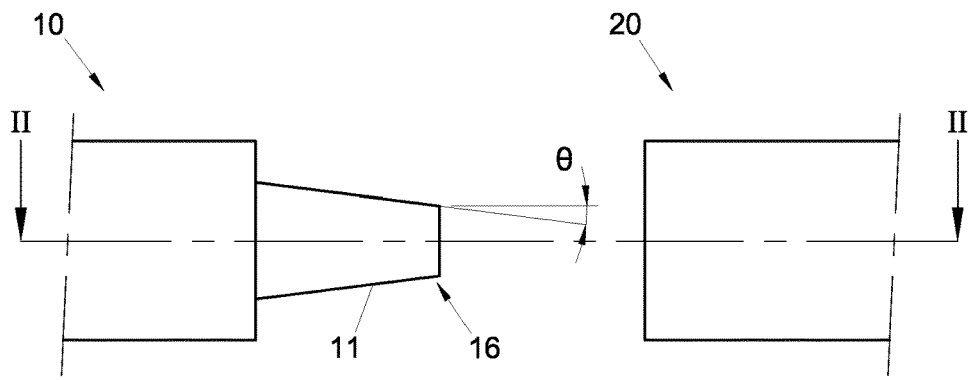
FIG. 1 shows a schematic side view of a male slip fitting and a matching female slip fitting both conforming to the ISO Luer Standard.
Figure 2:
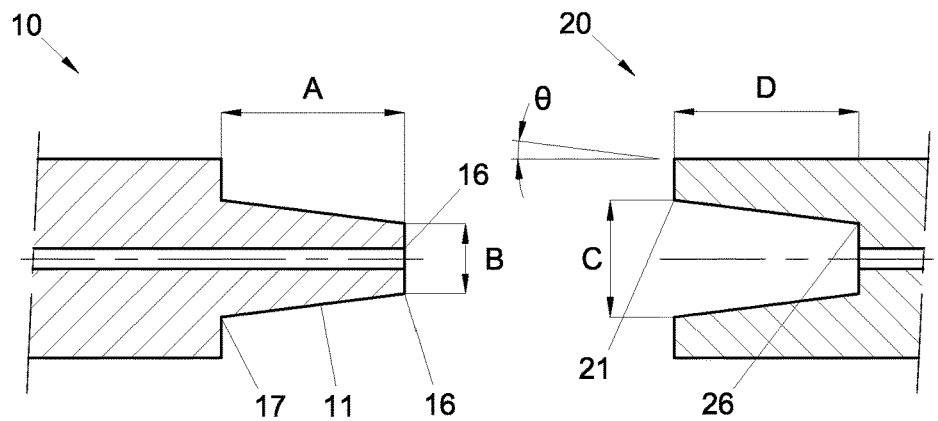
FIG. 2 shows a schematic sectional view II-II of the slip fittings of FIG. 1.
Figure 3:
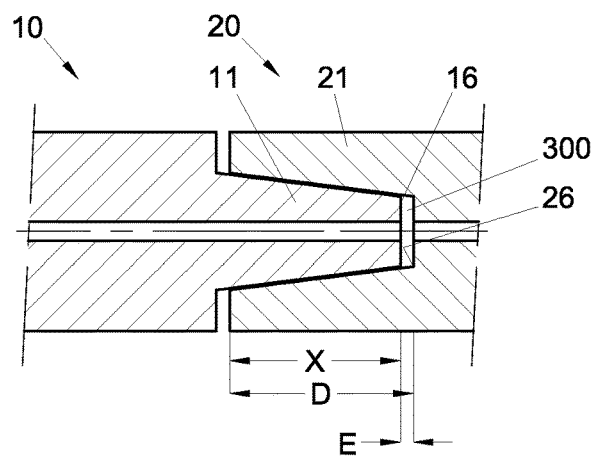
FIG. 3 shows a schematic sectional view II-II of the fittings of FIG. 1 in which the fittings are fully connected.
Figure 4:
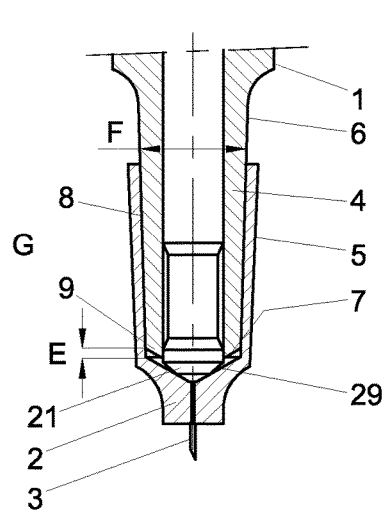
FIG. 4 shows a schematic sectional view of connected male and female slip fittings of an example of a syringe/conduit combination according to the invention.

In FIG. 4 a schematic sectional view of a distal portion of a syringe 1 having a male slip fitting 4 and a conduit part in the form of a needle assembly 2 having a female slip fitting 5 and a needle 3 is shown. The syringe 1 and the needle assembly 2 are connected to each other by a Luer slip fit type press fit connection between the male slip fitting 4 integrally forming a distal end portion of the syringe 1 and the female slip fitting 5 of the needle assembly 2. The male slip fitting 4 has an external frustoconical surface 6 with a distal end 7, and the female slip fitting 5 has an internal frustoconical surface 8 matching a portion of the external frustoconical surface 6 of the male slip fitting 4. The internal frustoconical surface 8 extends from an open proximal end of the female slip fitting 5 to an internal end 9 thereof defining an internal end surface 29 of the needle assembly 2.

The tightness of the slip fit connection between the male slip fitting 4 and the female slip fitting 5 is such that it can be established by application of an axial pressing force of 27.5 N for 5 s whilst twisting action torque does not exceed 0.1 Nm and resultant rotation does not exceed 90°. The male and female slip fittings 4, 5 are dimensioned to fit tight enough, to meet ISO Luer Standard requirements regarding resistance against axial removal forces to prevent inadvertent disconnection after the slip connection has been made.

Figure 5:
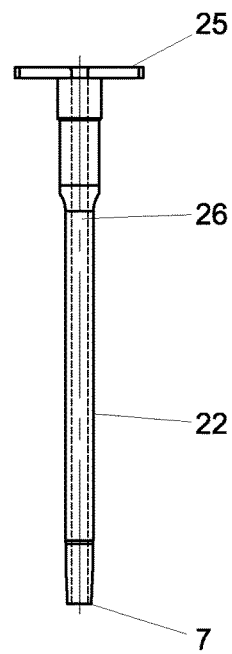
FIG. 5 shows a sectional view of a syringe part of the syringe/conduit combination according to FIG. 4.

According to the present example, the frustoconical surface of the male slip fitting 4 has a taper of about 3.44° (as indicated for the male slip fitting in FIG. 5). This taper is not in conformity with the ISO Luer Standard, but taper results in a reduced tolerance on the coupling distance E between the distal end 7 of the male slip fitting 4 and the bottom end 9 of the female slip fitting 5, in particular because the clamping pressure between the male fitting 4 and the female fitting 5 is applied closer to the internal end 7 of the female fitting where the walls of the fitting 5 are progressively more refrained from stretching radially outwardly by the connection to the internal end 7 as the distance to the internal end reduces to zero. In the present example, a coupling distance E of about 0.042 mm is obtained after the slip connection between the male and female slip fittings 4, 5 has been made. This coupling distance E results in a dead space volume 21 of about 0.01 ml.

In the present example, the female slip fitting is dimensioned to conform to all the respective requirements of the ISO Luer Standard, while the male fitting is designed according to the invention to depart from the ISO Luer Standard. In addition taking manufacturing tolerance ranges of the male and female slip fittings into account the inventive coupling distance E of less than 0.1 mm is obtained even with a diameter F of the male slip fitting 4 having the largest value within the respective tolerance range and with a diameter G of the female slip fitting 5 having a smallest value within the respective tolerance range. Although the female slip fitting is in conformity with the ISO Luer Standard, it is advantageous for further reducing the variation on the coupling distance E, that the female slip fittings are manufactured to tighter manufacturing tolerances than allowable under the ISO Luer Standard.

Figure 6:
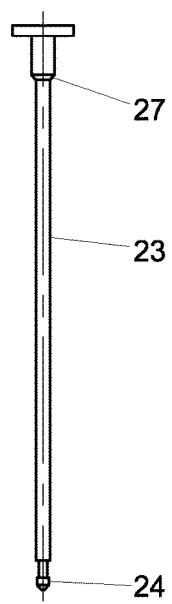
FIG. 6 shows a plunger of the of the syringe/conduit combination according to FIGS. 4 and 5.
Figure 7:
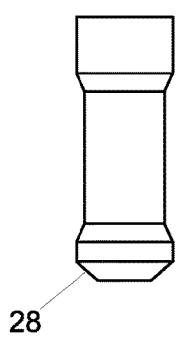
FIG. 7 shows a distal portion of the plunger of FIG. 6.
Figure 8:
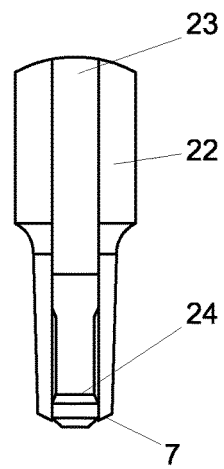
FIG. 8 shows a distal portion of only the syringe barrel and the plunger of FIG. 4 with the plunger is in its maximally inserted position.

The hollow barrel 22 integrally formed with the male slip fitting 4 of the syringe 1 is shown in FIG. 5. In FIG. 6, the plunger 23 of the syringe 1 is shown, while a distal end portion 24 of the plunger 23 is shown at an enlarged scale in FIG. 7. FIGS. 4 and 8 show a distal part of the syringe 1 with the plunger 23 in the maximally inserted position in which a free distal end portion 24 of the plunger 23 projects from the distal end 7 of the syringe 1. The dimensions indicated in FIGS. 5 to 7 relate to the presently most preferred embodiment, but as stated above these dimensions do not limit the scope of the present invention, and can be altered within the scope of the enclosed claims.

The syringe barrel 22 further has a flange 25 terminating the hollow barrel 22 at its proximal end and an internal conduit 26 of a constant cylindrical cross-section matching the cylindrical cross-section of the plunger 23 so that the plunger is in sealing contact with the inner wall of the conduit 26, and preferably slightly compressed to ensure a leak free sealing, when inserted therein. The portion of the conduit 26 with the cylindrical cross-section matching the cylindrical cross-section of the plunger 23 extends to the distal end, so that the distal end portion 24 of the plunger 23 can pass to a position projecting out of the distal end 7 of the syringe 1 up to a portion having a cross-section for sealing contact with the inner wall of the conduit 26, to ensure that no fluid remains in the conduit 26.

The plunger 23 has shoulder 27 near its proximal end. The flange 25 forming the proximal end of the hollow barrel 22 and the shoulder 27 of the plunger 23 constitute abutments limiting the distance over which the plunger 23 can be advanced in distal direction relative to the barrel 22, the shoulder 27 abutting against the proximal end of the hollow barrel 22 when the free distal end 24 thereof projects over a limited distance from the distal end 7 of the syringe as is best seen in FIG. 8. In addition, the axial length of the plunger 23 is such that after the slip connection between the male and female slip fittings 4, 5 has been made the free distal end of the plunger 23 at least as close to the internal end 9 of the female fitting 5 as the distal end 7 of the male fitting 4, but does not push the female fitting 5 and accordingly the needle assembly 2 off the male fitting 4 of the syringe 1. As is best seen in FIG. 4, this reduces the dead volume in the connection. The contour 28 of the free distal end of the plunger 23 partly matches the surface contour of the bottom 29 of the female slip fitting 5 to further minimize the dead volume while avoiding pushing the female slip fitting 5 off the male slip fitting 4.

Within the framework of the invention as set forth in the claims, many other embodiments and variants other than the embodiments and examples discussed above are conceivable. For example, the syringe part may have a female slip fitting and the needle part may have the female slip fitting. Also, the conduit part can for instance be part of a medical tubing, an I.V. bag or assembly, a catheter, a stopcock or an insulin pump or any other medical device which delivers a fluid through a conduit.

The invention claimed is:

1. A syringe/conduit combination comprising a syringe part and a conduit part connectable or connected to the syringe part;
    wherein one of said parts has a frustoconical male slip fitting and the other one of said parts has a female slip fitting having a frustoconical internal surface extending up to an internal end;
    wherein said male slip fitting is inserted or insertable into said female slip fitting establishing a press fitted connection with the male slip fitting axially extending up to an axial distance of less than 0.1 mm from the internal end of the female slip fitting;
    wherein a first liquid discharge channel extending through said male slip fitting and a second liquid discharge channel extending through said female slip fitting are in mutual serial communication for liquid transfer when said connection between said male and female fittings is established;
    wherein the syringe part comprises a hollow barrel and a plunger inserted into the hollow barrel from a proximal end, axially displaceable in the hollow barrel and sealingly fitting against an internal wall of the hollow barrel;

wherein the plunger and the hollow barrel have abutments limiting axial displacement of the plunger in a distal direction to a maximally inserted position; and wherein, when the male slip fitting is axially inserted into the female slip fitting, a distal end of the plunger when in its maximally inserted position is at an axial distance from an opposite one of the slip fittings that is equal to or less than the axial distance between the male slip fitting and the internal end of the female slip fitting.

2. A syringe/conduit combination according to claim 1, wherein the male slip fitting is axially inserted or insertable into the female slip fitting such that the male slip fitting is at an axial distance of less than 0.05 mm and preferably 0.042 mm or less from the internal end of the female slip fitting.

3. A syringe/conduit combination according to claim 1, wherein the male slip fitting is axially inserted or insertable into the female slip fitting such that the male slip fitting is in contact with the internal end of the female slip fitting.

4. A syringe/conduit combination according to claim 1, wherein the male slip fitting has a conical portion and a free end beyond the conical portion, said free end and the internal end of the female slip fitting having matching shapes such that when said free end of the male slip fitting is in contact with the internal end of the female slip fitting, substantially the entire surface of the free end of the male slip fitting is in contact with the internal end of the female slip fitting.

5. A syringe/conduit combination according to claim 1, wherein said plunger in its maximally inserted position projects distally from the fitting of the syringe part.

6. A syringe/conduit combination according to claim 1, wherein said plunger has a cross-section, wherein at least a portion of said internal wall of the hollow barrel has a cross-section sealingly fitting around the cross-section of the plunger, said portion extending up to the distal end of the syringe part.

7. A syringe/conduit combination according to claim 6, wherein said abutments limiting axial displacement of the plunger in a distal direction to a maximally inserted position are located proximally of said portion of said internal wall of the hollow barrel bounding said internal cross-section sealingly fitting around the cross-section of the plunger.

8. A syringe/conduit combination according to claim 7, wherein one of said abutments is constituted by the proximal end of the hollow barrel.

9. A syringe/conduit combination according to claim 1, wherein the male slip fitting is in conformity with the ISO-594/1 standard.

10. A syringe/conduit combination according to claim 1, wherein the female slip fitting is in conformity with the ISO-594/1 standard.

11. A syringe/conduit combination to claim 1, wherein said male slip fitting is connectable to said female slip fitting by application of an axial pressing force of 27.5 N.

12. A syringe/conduit combination according to claim 1, wherein the conical surface of the male slip fitting has a taper in the range between about 3° and 4°, preferably about 3.44°.

13. A syringe connectable to a conduit part, comprising:
a hollow barrel and a plunger inserted into the hollow barrel from a proximal end, axially displaceable in the hollow barrel and sealingly fitting against an internal wall of the hollow barrel;
a frustoconical male slip fitting or a frustoconical female slip fitting for establishing a press fitted connection with a matching female or, respectively, male fitting;
wherein a liquid discharge channel extending through said slip fitting for liquid transfer when said connection is established;
wherein the plunger and the hollow barrel have abutments limiting axial displacement of the plunger in a distal direction to a maximally inserted position; and
wherein a distal end of the plunger projects from the distal end of the fitting-hollow barrel when the plunger is in its maximally inserted position.

14. A syringe according to claim 13, wherein said plunger has a cross-section, wherein at least a portion of said internal wall of the hollow barrel has a cross-section sealingly fitting around the cross-section of the plunger, said portion extending up to the distal end of the syringe.

* * * * *